United States Patent [19]

Yamamoto

[11] Patent Number: 5,063,056

[45] Date of Patent: Nov. 5, 1991

[54] MELANOGENESIS-INHIBITING PREPARATION FOR EXTERNAL APPLICATION

[75] Inventor: Shinji Yamamoto, Fukuoka, Japan

[73] Assignee: Sansho Seiyaku Co., Ltd., Fukuoka, Japan

[21] Appl. No.: 526,354

[22] Filed: May 21, 1990

[30] Foreign Application Priority Data

Jun. 12, 1989 [JP] Japan .................................. 1-149833

[51] Int. Cl.$^5$ .......................... A61K 7/00; A61K 7/48
[52] U.S. Cl. ...................................... 424/401; 424/62; 514/21; 514/784; 514/460
[58] Field of Search .......................... 514/784, 21, 460; 424/401, 62

[56] References Cited

U.S. PATENT DOCUMENTS 4,545,982 10/1985 Takahashi ............................ 514/784
4,696,813 9/1987 Higa ...................................... 514/21
4,847,074 7/1989 Hatae .................................. 514/460

OTHER PUBLICATIONS

Merck Index, 10th Ed. (1983) p. 764, Kojic Acid Entry.

Primary Examiner—Thurman K. Page
Assistant Examiner—Robert H. Harrison
Attorney, Agent, or Firm—Jordan and Hamburg

[57] ABSTRACT

A melanogenesis-inhibiting preparation for external application contains 5-hydroxy-2-methoxymethyl-$\gamma$-pyrone as an active ingredient. The preparation is usable for the remedy of and prevention of chromatosis. It is applied to human skin in the form of a milky lotion, lotion, emulsion, ointment, cataplasm or cream.

3 Claims, No Drawings

MELANOGENESIS-INHIBITING PREPARATION FOR EXTERNAL APPLICATION

BACKGROUND OF THE INVENTION

1. Field of the Invention

The present invention relates to a melanogenesis-inhibiting preparation for external application, which contains 5-hydroxy-2-methoxymethyl-γ-pyrone as an active ingredient and which is effective for the remedy of and prevention of chromatosis such as chloasma (liver spots) and for whitening the human skin.

2. Prior Art

For a long time, a cosmetic material containing a peroxide such as hydrogen peroxide or zinc peroxide has been used, for the purpose of removing blotches such as spots or freckles which appear on the skin.

However, the peroxides are extremely unstable and, therefore, problems arise as to their storage stability. Additionally, stable incorporation of such a peroxide into a cosmetic base is difficult and the peroxides themselves do not have a sufficient whitening effect.

On the other hand, a cosmetic material containing vitamin C, cystein or colloidal sulfur has become utilized for the purpose of skin-whitening. However, the effect of such substances is still unsatisfactory.

Recently, kojic acid has been found to be effective as a substance for inhibiting formation of melanine in the human skin. Accordingly, a kojic acid-containing skin-whitening cosmetic material (Japanese Patent Publication No. 56-18569), a skin-whitening cosmetic material containing an ester of kojic acid with an aromatic carboxylic acid such as cinnamic acid or benzoic acid (Japanese Patent Publication No. 60-10005), and a skin-whitening cosmetic material containing an aliphatic carboxylic acid diester of kojic acid or an aliphatic carboxylic acid monoester of kojic acid (Japanese Patent Publication Nos. 61-60801 and 60-7961) have been proposed.

As mentioned above, kojic acid and kojic acid esters are known as excellent substances capable of inhibiting melanogenesis (formation of melanine). When a preparation of a cosmetic material or a medicine for external application formed to contain these substances as active ingredients is applied to the skin, an excellent whitening and melanogenisis-inhibiting effect are exhibited without injuries to the skin. Thus, kojic acid and kojic acid esters are known to be usable as an active ingredient for a cosmetic material or a medicine for external application.

However, other substances capable of inhibiting melanogenesis more effectively are strongly desired.

The object of the present invention is to provide a melanogenesis-inhibiting preparation for external application, which contains a substance having a higher melanogenesis-inhibiting activity than the above-mentioned kojic acid or derivatives thereof such as kojic acid esters.

In order to attain the above-mentioned object, the present inventors widely investigated and repeatedly studied various substances having a higher melanogenesis-inhibiting activity among kojic acid derivatives and, as a result, have found that 5-hydroxy-2-methoxymethyl-γ-pyrone which is a methyl ether of kojic acid has an extremely high tyrosinase activity-inhibiting effect and therefore has an effect of whitening B16 cells. On the basis of such findings, the present invention has been accomplished.

SUMMARY OF THE INVENTION

Accordingly, the present invention provides a melanogenesis-inhibiting preparation for external application, which contains 5-hydroxy-2-methoxymethyl-γ-pyrone as an active ingredient.

DESCRIPTION OF THE PREFERRED EMBODIMENTS

5-Hydroxy-2-methoxymethyl-γ-pyrone to be employed in the present invention is a known substance, as having been disclosed in N. S. Poonia et al., *J. Org. Chem.*, Vol. 42, page 2030, 1977.

The preparation for external application of the present invention is prepared by a known method, using 5-hydroxy-2-methoxymethyl-γ-pyrone as the active ingredient along with bases or agents which are generally employed in preparing ordinary preparations such as an emulsion, lotion, liniment or ointment.

The content of the active ingredient in the preparation of the present invention is from 0.001 to 20% by weight, preferably from 0.01 to 10% by weight, to the total weight of the preparation.

Next, some experimental examples demonstrating the melanogenesis-inhibiting activity of the preparation of the present invention will be described.

EXPERIMENTAL EXAMPLE 1

Tyrosinase Activity-Inhibiting Test:

A 30000G supernatant of mouse melanoma derived B16 cells (hereinafter referred to as "B16 cells") was used as a tyrosinase-containing liquid. 0.1 M phosphate buffer (pH 6.8) was used as a buffer, and the tyrosinase-inhibiting activity of test compounds was measured in accordance with the method mentioned below.

The above-mentioned tyrosinase liquid, buffer and 5-hydroxy-2-methoxymethyl-γ-pyrone having a determined concentration or an aqueous solution of the same were put in a container.

After 2 minutes, L-DOPA (0.1 M phosphate buffer, 10 mM DOPA) was added thereto, and the time-dependent variation of the absorbent ($\Delta OD$) at 475 nm at 37° C. was traced.

As a comparative test, a kojic acid solution was used and the time-dependent variation of the absorbance was measured in the same manner.

The results are shown in Table 1 below.

TABLE 1

| Compound Tested | Concentration (mM) | $\Delta OD$ 475 nm /10 min. |
| --- | --- | --- |
| 5-Hydroxy-2-methoxymethyl-γ-pyrone | 0.2 | 0.025 |
|  | 0.1 | 0.046 |
| Kojic Acid | 0.2 | 0.039 |
| Control | — | 0.147 |

As is obvious from the above-mentioned results, the active ingredient of the present invention of 5-hydroxy-2-methoxymethyl-γ-pyrone has an about a two-time faster velocity inhibiting activity than the comparative kojic acid.

EXPERIMENTAL EXAMPLE 2

B16 Cells-Whitening Test:

5-Hydroxy-2-methoxymethyl-γ-pyrone was added to a fetal calf serum-containing Eagle MEM medium, in a concentration of 2.5, 1.25, 0.63 or 0.31 mM. On the other hand, kojic acid was added to the same medium in a concentration of 2.5 or 1.25 mM, for comparison. B16 cells were inoculated into each liquid medium in an amount of $1 \times 10^5$. The liquid medium was exchanged for a fresh one after 4 days, and cell pellets were prepared after 5 days. The whiteness of the pellets was observed by naked eye.

The results obtained are shown in Table 2 below.

TABLE 2

| Compound Tested | Concentration (mM) | Cell-Whitening Degree |
|---|---|---|
| 5-Hydroxy-2-methoxymethyl-γ-pyrone | 1.25 | 3+ |
| | 0.63 | 2+ |
| | 0.31 | 1+ |
| Kojic Acid | 2.5 | 3+ |
| | 1.25 | 2+ |
| Control | — | — |

As is obvious from the above-mentioned results, active ingredient of the present invention of 5-hydroxy-2-methoxymethyl-γ-pyrone shows the same cell-whitening effect as the comparative kojic acid even though the evaluating concentration of the former is about ½ that of the latter. Further, the former shows an about 2 times higher whitening effect than the latter.

Next, examples of the present inventions are mentioned below.

EXAMPLE 1

(Milky Lotion)

| Ingredients (parts by weight): | |
|---|---|
| (A) Polyoxyethylene Glycol Monostearate (40 E.O.) | 2.00 |
| Self-emulsifying Glycerin Monostearate | 5.00 |
| Stearic Acid | 5.00 |
| Behenyl Alcohol | 1.00 |
| Liquid Paraffin | 1.00 |
| Glycerin Trioctanoate | 10.00 |
| Antiseptic | proper quantity |
| Perfume | proper quantity |
| (B) 1,3-Butylene Glycol | 5.00 |
| 5-Hydroxy-2-methoxymethyl-γ-pyrone | 0.50 |
| Pure Water | balance |

The components of (A) are heated and dissolved to form an oily phase. Separately, the components of (B) are heated and dissolved to form an aqueous phase.

The aqueous phase is added to the oily phase, stirred, emulsified and cooled to obtain a milky lotion.

EXAMPLE 2

Lotion

| Ingredients (parts by weight): | |
|---|---|
| (A) Polyoxyethylene-Hardened Castor Oil (60 E.O.) | 1.00 |
| Ethanol | 15.00 |
| Citric Acid | 0.10 |
| Sodium Citrate | 0.30 |
| 1,3-Butylene Glycol | 4.00 |
| 5-Hydroxy-2-methoxymethyl-γ-pyrone | 0.50 |
| Antiseptic | proper quantity |
| Perfume | trace |
| Pure Water | balance |

The components are uniformly stirred, mixed and dissolved to obtain a lotion.

EXAMPLE 3

Emulsion

| Ingredients (parts by weight): | |
|---|---|
| (A) Polyoxyethylene Behenyl Ether (20 E.O.) | 0.50 |
| Polyoxyethylene Sorbitol Tetraoleate (60 E.O.) | 1.00 |
| Oleophilic Glycerin monostearate | 1.00 |
| Stearic Acid | 0.50 |
| Behenyl Alcohol | 0.50 |
| Avocado Oil | 1.00 |
| Antiseptic | proper quantity |
| Perfume | trace |
| (B) 1,3-Butylene Glycol | 5.00 |
| Carboxyvinyl polymer | 0.10 |
| 2-Hydroxy-5-methoxymethol-γ-pyrone | 0.10 |
| Pure Water | balance |

The components of (A) are heated and dissolved to prepare an oily phase. Separately, the components of (B) are heated and dissolved to prepare an aqueous phase.

The aqueous phase is added to the oily phase, stirred, emulsified and cooled to obtain an emulsion.

EXAMPLE 4

Ointment

| Ingredients (parts by weight): | |
|---|---|
| (A) Polyoxyethylene Sorbitan Monostearate (60 E.O.) | 1.00 |
| Polyoxyethylene Sorbitol Tetraoleate (60 E.O.) | 1.50 |
| Self-emulsifying Glycerin Monostearate | 1.50 |
| Glycerin | 1.50 |
| Bleached Bee's Wax | 2.00 |
| Paraffin | 2.00 |
| Stearic Acid | 3.00 |
| Behenyl Alcohol | 3.00 |
| Liquid Paraffin | 5.00 |
| Antiseptic | proper quantity |
| Perfume | trace |
| (B) 1,3-Butylene Glycol | 5.00 |
| Citric Acid | 0.30 |
| 2-Hydroxy-5-methoxymethyl-γ-pyrone | 1.00 |
| Pure Water | balance |

The component of (A) are heated and dissolved to prepare an oily phase. Separately, the components of (B) are heated and dissolved to prepare an aqueous phase.

The aqueous phase is added to the oily phase, stirred, emulsified and cooled to obtain an ointment.

| Ingredients (parts by weight): | |
|---|---|
| (A) Polyacrylic Acid | 30.00 |
| 5-Hydroxy-2-methoxymethyl-γ-pyrone | 10.00 |
| Sorbitan Monooleate | 1.00 |
| Pure Water | 30.7 |
| (B) Sodium Polyacrylate | 7.00 |
| Aluminum Chloride | 0.30 |
| Concentrated Glycerin | 20.00 |
| Titanium Oxide | 1.00 |

The components of (A) are heated and dissolved. Separately, the components of (B) are heated and dissolved. (B) is added to (A), stirred and mixed to obtain a cataplasm material.

EXAMPLE 6

(Cream):

| Ingredients (parts by weight): | |
| --- | --- |
| 1. Polyethylene Glycol Monostearate (40 E.O.) | 2.00 |
| 2. Self-emulsifying Glycerin Monostearate | 5.00 |
| 3. Stearic Acid | 5.00 |
| 4. Behenyl Alcohol | 1.00 |
| 5. Liquid Paraffin | 10.00 |
| 6. Glyceryl Trioctanoate | 10.00 |
| 7. Paraoxybenzoate | 0.20 |
| 8. 1,3-Butylene Glycol | 5.00 |
| 9. Disodium Edetate | 0.01 |
| 10. 5-Hydroxy-2-methoxymethyl-γ-pyrone | 5.00 |
| Pure water to make | 100 |

Manufacturing Method:

(A) (1) to (6) are heated and dissolved.
(B) (7) to (10) are heated and dissolved.
(C) (B) is added to (A), emulsified, stirred and cooled.

Direction and Dosage:

A proper amount of the cream is applied to and rubbed on the face.

As mentioned above, the present invention provides an excellently useful melanogenesis-inhibiting preparation for external application which exhibits the noticeable melanogenesis-inhibiting effect and is almost non-toxic and, further, has a low coloring property.

While the invention has been described in detail and with reference to specific embodiments thereof, it will be apparent to one skilled in the art that various changes and modifications can be made therein without departing from the spirit and scope thereof.

What is claimed is:

1. A preparation for external application to skin to inhibit melanine formation comprising 5-hydroxy-2-methoxymethyl-γ-pyrone as an active ingredient, said active ingredient being present in an amount ranging from 0.001 to 20% by weight of the total amount of said preparation, said preparation being in a form selected from the group consisting of lotions, emulsions, ointments, cataplasms and creams to be applied to human skin.

2. A preparation as in claim 1, wherein said active ingredient is present in an amount ranging from 0.01 to 10% by weight of the total amount of said preparation.

3. A preparation as in claim 1, wherein said lotion is a milky lotion.

* * * * *